(12) United States Patent
Kappelhof et al.

(10) Patent No.: US 7,494,505 B2
(45) Date of Patent: Feb. 24, 2009

(54) METHOD AND DEVICE FOR MANIPULATION OF AN INTRAOCULAR LENS

(75) Inventors: John A. Kappelhof, Carlsbad, CA (US); Jos van Loobergen, Hoogeveen (NL); Jon Taylor, Gorton, MA (US); Kevin J. Ehrenreich, Birnamwood, WI (US); Robert M. Kershner, Boston, MA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 587 days.

(21) Appl. No.: 10/622,988

(22) Filed: Jul. 18, 2003

(65) Prior Publication Data

US 2005/0277944 A1    Dec. 15, 2005

Related U.S. Application Data

(60) Provisional application No. 60/398,821, filed on Jul. 26, 2002.

(51) Int. Cl.
  *A61F 2/06*    (2006.01)
(52) U.S. Cl. ................................. 623/6.12; 606/107
(58) Field of Classification Search .................. None
  See application file for complete search history.

(56) References Cited

U.S. PATENT DOCUMENTS 5,190,552 A * 3/1993 Kelman ..................... 606/107

(Continued)

FOREIGN PATENT DOCUMENTS

EP    1114623    7/2001

(Continued)

*Primary Examiner*—Todd E Manahan
*Assistant Examiner*—Tuan V. Nguyen
(74) *Attorney, Agent, or Firm*—Advanced Medical Optics, Inc.

(57) ABSTRACT

A method for charging a deformable intraocular lens into a receptacle through a slit or opening in the receptacle periphery, the lens in un-deformed state comprising a) a roughly disc shaped optic part configured to act as a lens when inserted into an eye and b) at least two elongated haptic legs, each leg having an inner end attached to the optic part, an outer end being free and intermediate points in between the inner end and the free end, each leg being curved in unstressed state and being flexible to at least a less curved configuration under stress. The method comprises the steps of i) stretching the legs to align the legs along a substantially straight line, ii) aligning or maintaining the substantially straight line over and substantially parallel with the slit or opening of the receptacle, and iii) transferring at least the two legs through the slit or opening into the receptacle. A device for stretching the haptics of a lens comprises i) at least two haptic guiding surfaces arranged for each of the at least two haptic legs, the guiding surfaces having less curvature than the legs in un-stressed state, ii) a seat for the lens arranged with respect to the guiding surfaces so as to allow, when a lens is positioned in the seat, contact between a first point on the leg and its guiding structure and iii) a lens guiding arrangement allowing the lens to be moved along a path bringing at least a second point on the leg into contact with, or closer to, its guiding structure or a transfer opening allowing passage of the lens with the haptics, having said less curvature, to a receptacle.

30 Claims, 4 Drawing Sheets

U.S. PATENT DOCUMENTS

| | | | | |
|---|---|---|---|---|
| RE34,424 E | * | 10/1993 | Walman | 623/6.54 |
| 5,281,227 A | * | 1/1994 | Sussman | 606/107 |
| 5,497,974 A | * | 3/1996 | Tapang | 249/74 |
| 5,556,400 A | * | 9/1996 | Tunis | 606/107 |
| 6,083,231 A | | 7/2000 | Van Noy et al. | |
| 6,129,733 A | * | 10/2000 | Brady et al. | 606/107 |
| 6,537,282 B1 | * | 3/2003 | Pynson et al. | 606/107 |
| 6,607,537 B1 | * | 8/2003 | Binder | 606/107 |

FOREIGN PATENT DOCUMENTS

WO     WO 9812969     4/1998

* cited by examiner

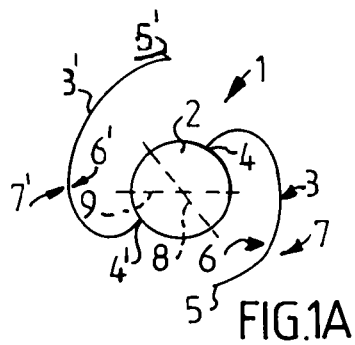
FIG.1A
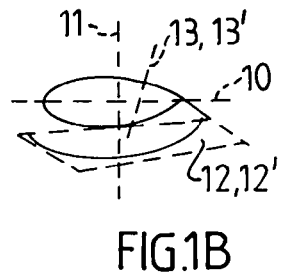
FIG.1B
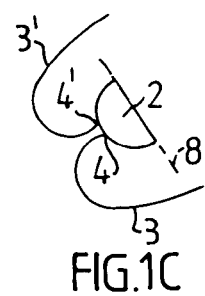
FIG.1C
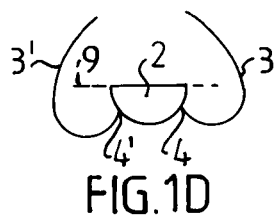
FIG.1D
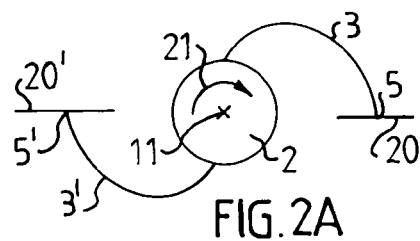
FIG.2A
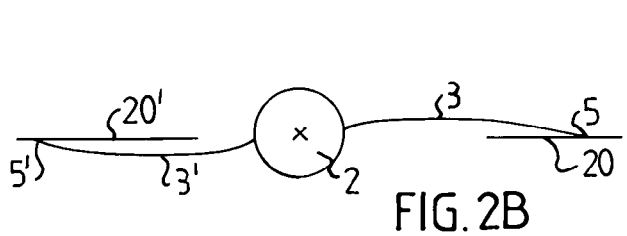
FIG.2B    FIG. 2C
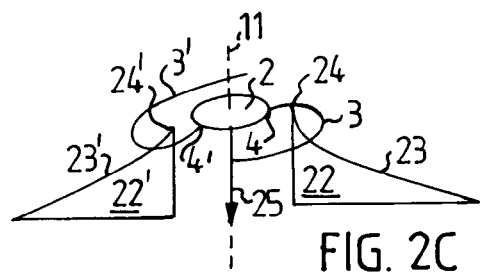
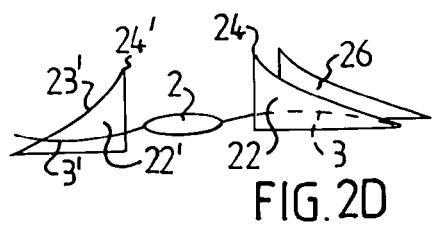
FIG.2D
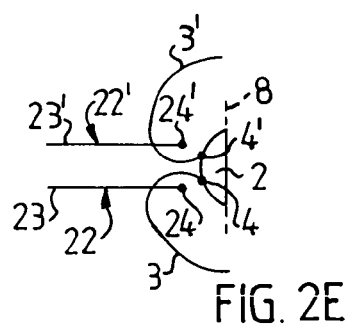
FIG. 2E
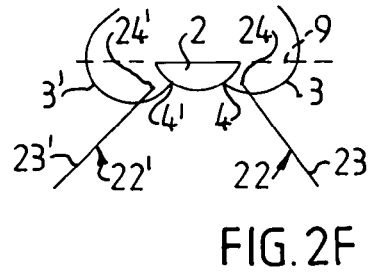
FIG.2F
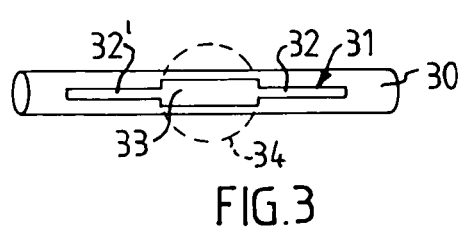
FIG.3

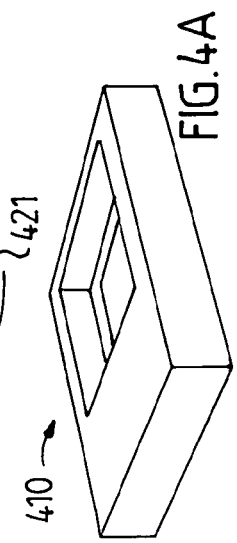
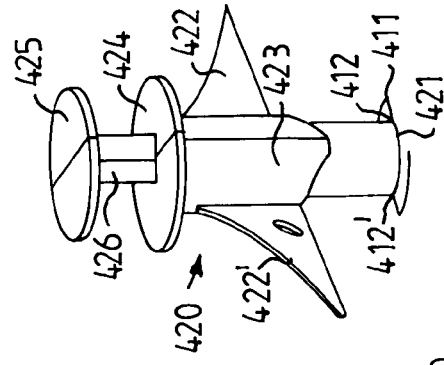
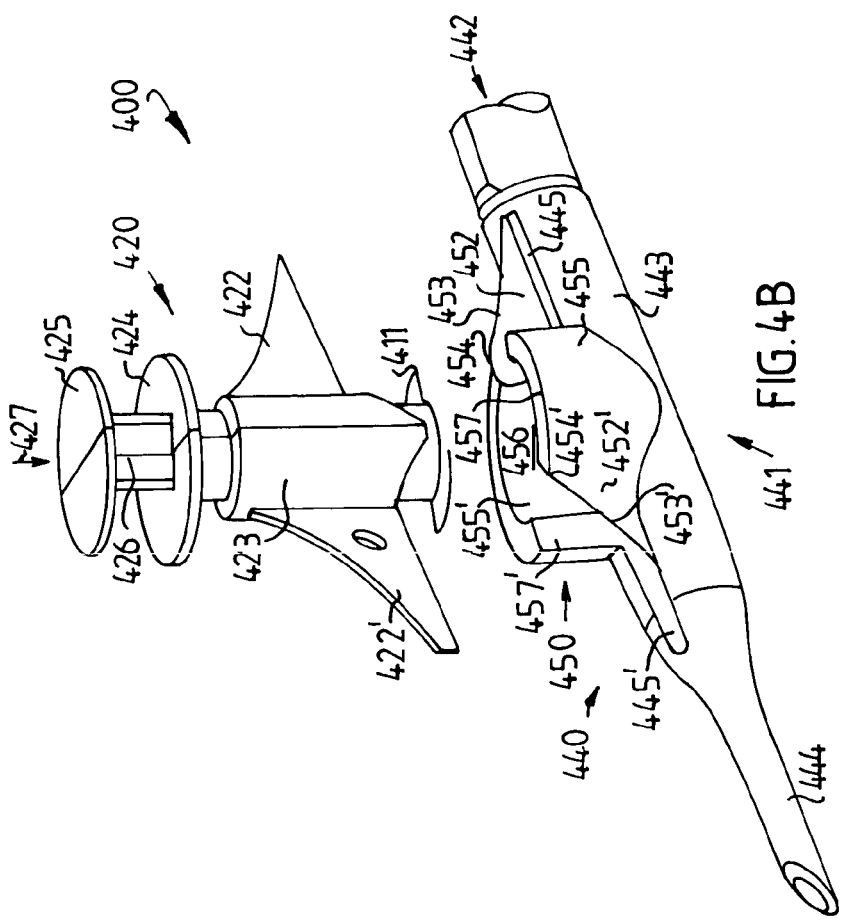
FIG. 4A
FIG. 4B

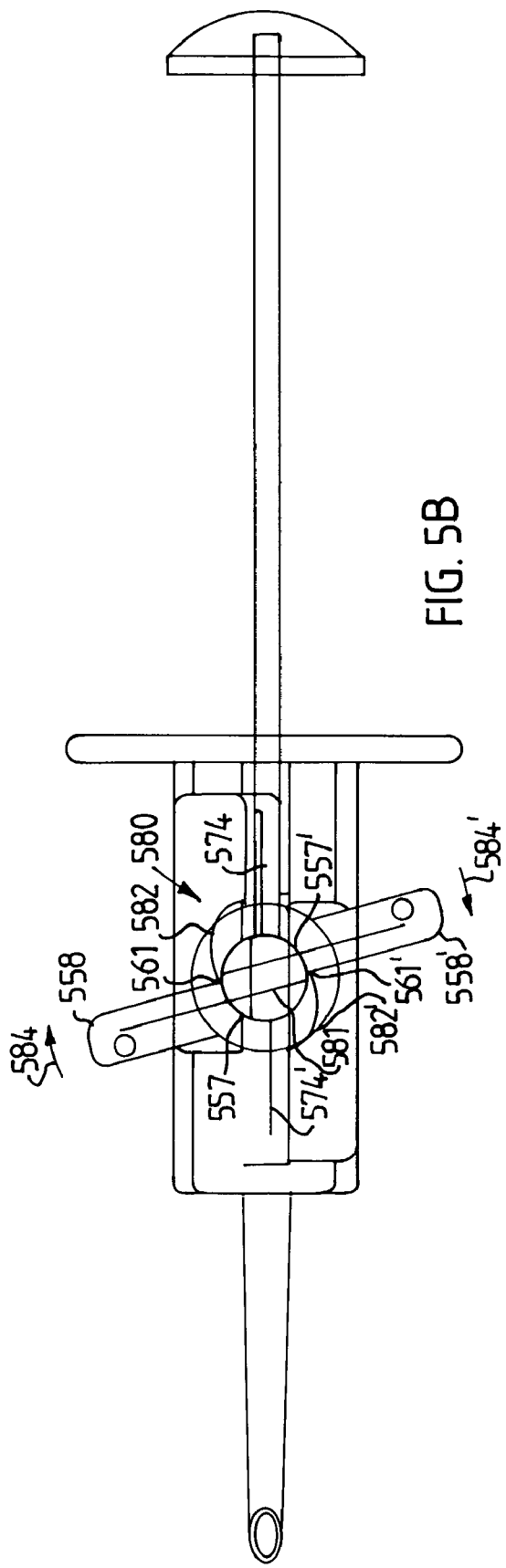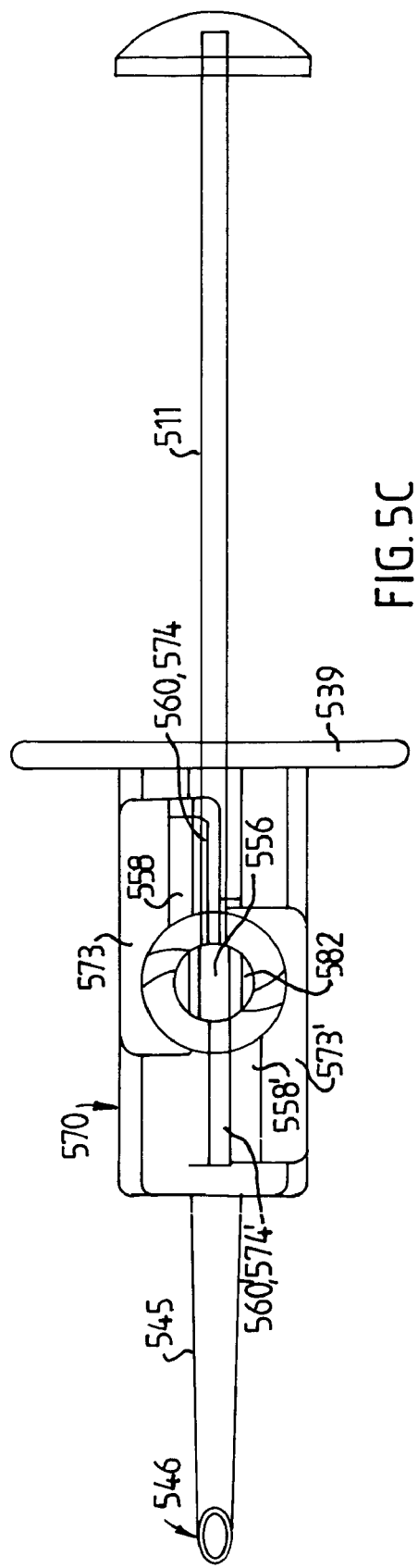

METHOD AND DEVICE FOR MANIPULATION OF AN INTRAOCULAR LENS

RELATED APPLICATION

The present application claims priority under 35 U.S.C. §119 of U.S. application Ser. No. 60/398,821 filed Jul. 26, 2002.

TECHNICAL FIELD

The present invention relates to a method and a device for manipulation of and in particular stretching the haptics of a deformable intraocular lens, the lens in un-deformed state comprising a) a roughly disc shaped optic part, defining an optic plane and a concentric optic axis normal to the plane, configured to act as a lens when inserted into an eye and b) at least two elongated haptic legs, each leg having an inner end attached to the optic part, an outer end being free and intermediate points in between the inner end and the free end, each leg being curved in unstressed state, the curvature defining a curve plane for each leg, and being flexible to at least a less curved configuration under stress.

BACKGROUND

Deformable intraocular lenses are used both for replacement of the natural lens in cataract afflicted eyes and for surgical implantation of an additional lens for refraction correction purposes. In a typical cataract operation the eye ball is punctured close to the limbus and an instrument is inserted and used to disintegrate and remove the opaque eye lens. Next an artificial lens is inserted through the incision to replace the natural lens and is kept in place, normally in the posterior chamber, by haptics in the form of either flexible wings (one piece lens) or flexible spiraling legs (two or more piece lenses) later developed for better stabilization in the eye. Healon(R) or a similar agent is introduced during both steps in order both provide bulk and protect sensitive tissue during the operation. The procedure is about the same for phakic corrective lenses although the natural lens is normally not removed and the thinner lenses can be located also in the anterior chamber in front of the iris.

The eye incision size necessary is determined by the lens size and the first generation of hard lenses, typically made from PMMA, required a cut corresponding to the lens diameter. Soft lenses have been developed for the purpose of limiting the incision needed to insert the lens in the eye, thereby reducing the risks for eye ball distortions and infections and improving post-operative healing. The soft lens, e.g. made from silicone, can be folded or rolled to a fraction of its initial diameter and then regains its original shape within the eye. Yet, manual folding followed by insertion, release and manipulation of the lens through the minimal incision requires the physician to execute high skill and various tools have been developed and marketed to facilitate these steps. Typical general problems include the establishment and maintenance, without tearing, of the small incision not to introduce deformation and subsequent astigmatism, not to touch the cornea or the thin endothelial cell layer, to control the positioning of both lens optic part and especially the flying haptics and to avoid any infection or introduction of debris into the eye.

Although the deformable lenses have solved a lot of problems, other are introduced instead. The lens material is softer and more susceptible to damage, cutting or shear by hard or sharp parts or imperfections in implanters or other manipulating devices, problems exaggerated by the material friction making the material easily caught in tolerances necessarily present between device parts. Also the lens haptic parts need consideration. The lens has to be folded or deformed so as to avoid collision or overlap between the haptics and their anchoring points in particular, yet not so far separated that a plunger attacks directly thereon. It has to be folded not to be damaged during transport and to be released and unfolded properly at exit. Most lenses are asymmetrical with a distal and a proximal side and need to be ejected in proper oriented in the eye. Yet the very necessity that the haptics are the most peripheral lens parts makes them especially exposed and, furthermore, force applied thereto give high torque and twisting moment to the lens, easily resulting in misalignment or rotation of the whole lens, in turn resulting in improper folding or deformation, damage to haptics or optics and improper release at exit, all most often manifested in abnormally high displacement resistance.

These soft lens characteristics put severe demands on any device for their manipulation and implanters with lens transportation channels in particular. The overall demand on such a channel is that it should be smooth not to impose shear, friction, grinding, cutting or pinch to the lens optic or haptic and this applies both to any transition in monolithic channel parts and to joints in multiple part channels, the latter to be avoided as far as possible as grades and misalignments are almost inevitable unless instead the parts are fused, polished and finally cleaned to avoid any trace of debris. Yet multiple parts may be unavoidable, e.g. when providing for doors or closures to allow lens insertion or when using cartridge type inserts for lenses deformed by separate or external means. In general the lens transport through the channel comprises at least two distinct phases. In a first phase the lens is transported, possibly under complete or partial deformation, to a stand-by position, ready for release, close to the end of an elongated tip designed for insertion through the incision into the eye, although this phase is commonly performed before the tip has been inserted into the eye. In a second phase, performed with the tip inserted into the eye, the lens is pushed the remaining short distance out from the stand-by position for released in the eye. A plunger arrangement need to cope with the different requirements in these phases, the first in general needing a slow but steady force and speed not to stress the lens whereas the second is more of a short triggering action as the lens tend to unfold automatically at the end tip due to its stored elastic energy. The force variations are considerably more pronounced in the first phase if a lens deformation takes place, increasing until completion of deformation and then dropping, and in the second phase if the tip is designed with deformation features or release features, e.g. slits. In manual operation force drops may easily result in inadvertent displacements, especially disastrous at final release. Lens deforming convergent channels poses additional problems, e.g. in respect of controlled initiation as well as continued folding, especially in view of the haptic problems outlined. The problems tend to be more pronounced for the two or more piece lenses with their delicate and elusive spiralling haptics compared to the more sturdy and localized single piece haptics.

Although many tool types have been proposed it is believed that no suggestion meets the abovesaid requirements to any acceptable extent. Early device suggestions were merely auxiliary fixtures or jigs for assisting forceps or hook handling of the lenses, as exemplified by U.S. Pat. No. 4,702,244, U.S. Pat. No. 5,100,410 and U.S. Pat. No. 5,176,686 but neither high deformation degrees nor small incisions could be obtained or acceptable manipulation control. Many later proposals rely on separate means for lens deformation and lens transportation respectively, e.g. jaws, paddles, e.g. U.S. Pat. No. 4,880,000, or deformation members acting lateral to the channel. Such devices necessarily comprises several parts between which the lens is deformed, and the lens deformed between such parts is often inserted as a cartridge into a reusable implanter device, all parts tending to introduce the potentially harmful imperfections described. Moreover, such devices rely on operator skill, rather than assistance by convenient device safety features, for correct lens insertion and manual deformation, easily resulting in arbitrary and inconsistent folding and release behavior. As a typical example the U.S. Pat. Nos. 5,494,484 and 5,800,442 relate to a device for lens deformation between two hinged half tube, wherein skill is required not to invoke random results or pinching of optic or haptic. Although the already deformed lens should allow for a simple plunger advancement mechanism a screw arrangement is used, requiring an impractical two hand operation in the critical moment of lens release. Numerous proposals have also been made for devices with convergent channels in which the lens is folded and deformed during forward transport in the channel before final release at the end. The lens may be inserted flat or slightly bent at the channel entrance for further downstream deformation, proper folding frequently assisted by grooves or other structures in the convergent channel parts. Typical examples are disclosed in U.S. Pat. No. 4,919,130, U.S. Pat. No. 5,275,604, U.S. Pat. No. 5,474,562, U.S. Pat. No. 5,499,987, U.S. Pat. No. 5,584, 304, U.S. Pat. No. 5,728,102, U.S. Pat. No. 5,873,879 (WO96/03924), DE 3610925, WO 96/20662 and WO 96/25101. Although such deformation devices may require less operator skill the results are far from satisfactory and consistent. As said, the transport deformation principle requires high and varying transportation forces, increasing stress and possible damage of the lens from channel and plunger. A further cause of lens damage is the fact that such devices have a larger entrance than exit channel cross-section, the added area sometimes added to facilitate insertion of the unstressed lens but always needed to accommodate the plunger cross-section area in the height direction. Shear between channel and plunger is then unavoidable where the cross-section decreases or changes, often causing squeezing or even cutting of the soft lens material in addition to the potentially destructive point force applied between the plunger and the non-deformed lens. Also the initially unfolded lens is highly susceptible to misalignment due to the twisting forces described, often resulting in improper folding and later unfolding or damage to the displaced optic or haptic, in spite of extensive means proposed to accommodate and protect the haptic during lens pushing. Also the problem of convenient use of the device in view of the strongly varying force requirements remains unsolved as well as the risk for actual implantation of a damaged lens due to the masking effect of uncontrolled force variations.

As indicated special problems are experienced with the two or more piece lenses having spiraling haptics with extended flexible legs wherewith one end attached to the lens optic part and the other end free. Many of these problems are associated with the mobility of such haptics and the difficulties involved in the giving the haptics a proper initial orientation. Typically the haptics have a curvature in un-stressed condition extending a bit out from and around the edge or periphery of the lens optic part to remain outside the optically active area also after some radial fixation compression when inserted in the eye. The peripheral location makes the haptic exposed and its curvature inconsistent with the highly compressed state of the deformable lens prior to release in the eye. Normally the haptics have to be carefully oriented, e.g. both forward or one forward and one rearward with respect to an implanter duct, and also stretched to a less curvature to fit within the duct boundaries. Often the haptics are manually oriented with assistance of only simple tools, such as forceps, even when placed in implanters otherwise highly sophisticated in respect of lens folding and handling features. Manual manipulation means risk for faulty or irreproducible results, especially as different implanters and even lens types or diopters may require different approaches. Accordingly there remains a need for methods and means assisting haptic manipulation.

SUMMARY OF INVENTION

A main object of the present invention is to avoid the problems with hitherto used methods and means for manipulation of intraocular lenses. More particularly an object is to improve manipulation of spiraling haptic types. Another object is to reduce risks for lens damage, faulty operation and non-reproducible results. Still another object is to offer improvements useful for different lenses and implanters. Yet an object is to reduce the need for skill in manual operating steps. A further object is to offer possibilities for various final haptic configurations. Still an object is to facilitate transfer of the manipulated lens to various receptacles such as lens cassettes and implanters. A further object is to provide devices for these purposes, which are simple and inexpensive and possible to use as a disposable or single-use device.

These objects area reached with the characteristics set forth in the appended patent claims.

By use of a device adapted for haptic manipulation the manual intervention can be reduced. Guiding structures assist in controlling haptic stretching by in a sense serving as a template for haptic final curvature or its process of stretching. When each haptic leg has its own guiding structure it becomes possible to control each leg independently, e.g. for different requirements on front and rear haptics in an implanter duct, and to allow stretching of the legs sequentially or simultaneously, the latter making the haptic manipulation a single step operation. It also means that the lens can be held fixed in its final configuration, e.g. allowing the lens to be stored in the device, attached to various secondary devices such as lens cassettes or implanters etc. The guiding structures are compatible with several haptic configurations, such as concentric, parallel or angled as well as pointing in the same or opposite directions, enabling transfer of the manipulated lens through similarly shaped openings to various receptacles. By arrangements for lens movement relative the guiding structures it is possible to manipulate the haptics by movement of the lens, offering a larger and more localized action point as compared to the flying haptics and also avoiding interference with the guiding structure area. If desired a single lens movement can be used to affect all haptics in a single operation. It is also possible to combine or unite the lens movement with movements for folding or transferring the lens to receptacles. A suitable method is to stretch two haptics to align them into a substantially straight line and then transfer the lens through an elongated slit of a receptacle when being kept in parallel with the line. In this way it is avoided that the haptics need to be manipulated when in the receptacle. The lined up configuration is highly compatible with charging of the lens into a lens-transporting duct as in lens implanting or compressing devices.

Further objects and advantages with the invention will be evident from the detailed description hereinbelow.

DETAILED DESCRIPTION

General

In the absence of explicit statements to the contrary, as used herein expressions like "comprising", "including", "having", "with" and similar terminology shall not be understood to be exclusively restricted to recited element but shall be understood to allow for the presence of further elements as well and shall be understood to cover any element in integral, subdivided or aggregate forms. Similarly, expressions like "connected", "attached", "arranged", "applied", "between" and similar terminology shall, not be understood to cover exclusively direct contact between the recited elements but shall be understood to allow for the presence of one or several intervening elements or structures. The same applies for similar expressions when used for description of forces and actions.

Also as used herein, and unless otherwise indicated, positional and directional statements for device, such as "axial", "front" and "rear" and "forward" and "rearward", shall be understood with reference to the lens delivery direction when injected into an eye, i.e. the transport direction of the lens in an implanter duct. The device "axial" direction shall be understood as a line centered in the lens duct, although such an axis need not always be entirely straight but can be curved, e.g. in convergent type ducts where the duct may have a varying cross-section shape.

The invention described herein can be used for most existing intraocular lenses as superficially described in the introduction, either for cataract or for corrective purposes. It can be used also for manipulation of haptics for hard lenses but preferably the lens is deformable. The lenses generally comprise an optic part and a haptic part. The optic part provides the refractive properties and can have any desired optic property, such as strongly positive refraction for replacement of the natural lens or positive or negative refraction to any degree for corrective purposes. The optic part is generally lens shaped but can have other initial forms, e.g. bag form for after-filling with refractive liquid or mass, other forms for re-shaping or cross-linking within the eye or pre-deformed lenses with memory for recovery of the memorized form in the eye. The optical part edge can be sharp, blunt or flat. The haptic part serves the purpose of contacting the eye inner circumference so as to center and stabilize the optical part in the eye. Although haptics are known being formed as flat wings extending from the optical parts or similarly shaped loops, the invention is mainly related to the having at least one, but normally two or sometimes more, flexible legs spiraling around the optical part. The invention is compatible with most such haptic types although most preferably the haptics is of the kind described in the introduction, extending out from and at least partly around the periphery of the optic part. Also the anchoring between haptic and optic can be of somewhat different design, e.g. "tangential" when the curved part of the haptic extends directly out from the optic disc substantially tangentially or "radial" when there is a more or less straight part extending substantially radial out form the optic disc and to whose outer end the curved part is attached, such designs being fully consistent with the present invention.

A soft lens may be given a reduced diameter, suited for insertion in a small eye incision, in a number of different ways, known per se, e.g. rolled to spiral form, single or multiple folded to various forms of single or multiple overlap or bellow shape, radially deformed or stretched under axial expansion or elongation etc. and in reality any method used normally will involve several pure size reduction principles. As used herein, expressions like "folding", "deforming", "compressing", etc. are used interchangeably to indicate any kind of size reduction method for implantation purposes and shall not be understood to be limited to any particular method, unless otherwise specifically indicated or explicitly described. To be useful the shape change shall be temporary so as to allow the lens to regain it original shape in the eye and preferably the lens is elastically deformed so as to automatically return to its original shape under non-stressed conditions. Conversely, any major permanent deformation is normally equivalent to a damage of the lens. Typically the incision in the eye is a straight cut with a length between 1 and 6 mm, preferably between 2 and 4 mm, which is laterally widened into a more rounded hole and the lens shape after deformation should be adapted for introduction through such an incision, typically with a generally cylindrical outer surface, possibly slightly flattened into a more elliptical form.

Similarly the haptics of the lens normally have a well-defined initial configuration as well as a well-defined final configuration when implanted in the eye, with only slightly flexed haptics to create a fixation pressure against the eye interior. However, during the implantation operation the haptics may be subjected to severe deformation stress depending on the implantation method used. Especially at compression of deformable lenses the haptics may have to be intentionally deformed, e.g. to conform to a transportation duct or squeezed between folds in the optic part or against the duct wall when subjected to the lens compression forces. For such deformations as well as the controlled manipulations of the present invention expressions like "stretching", "flexing", "bending", "stressing", etc. are used interchangeably. Reference will also be made to the haptic "curvature" and a "curve plain" being a flat plane drawn to roughly contain the linear extension of the haptic. For the un-stressed lens such planes are frequently also roughly perpendicular to the optic disc although slight deviations exist, e.g. a somewhat twisted attachment to the optic disc, also meaning that the planes for all haptics need not necessarily coincide or being parallel.

The device according to the present invention can be said to include basically a) haptic guiding surfaces, b) a seat for the lens and c) a lens guiding arrangement allowing movement of the lens, these component being generally described earlier.

The Guiding Surfaces

The guiding surfaces shall have at least one surface component perpendicular to the haptic plane, when the lens is positioned in the seat, and an in-plane extension, i.e. its extension in or parallel with the haptic plane, sufficient for at least contacting one point, a "first point", along the haptic leg. The point is preferably close to or at the free end or close to or at the inner end when the haptic is in the unstressed condition. Preferably the in-plane extension coves a major length, more preferably substantially the whole length between the inner end and the free end and most preferably a length corresponding to the haptic length in stretched straight condition. Over such lengths the surface shall have a less curvature than the haptic legs in unstressed condition, preferably substantially straight and most preferably straight, in order to be able to make contact with, or come closer to, at least one haptic point, a "second point", and preferably more intermediate points, between the inner end and the free end of the haptic leg, during the stretching process. The surface component normal extension, i.e. its extension perpendicular to the haptic plane, should have a minimum height sufficient for safely guiding the first point with respect to displacement in the normal direction. If the lens is arranged movable in the normal direction it is preferred that the height covers at least a part of the normal mobility, more preferably a major part and most preferably substantially the whole of the normal mobility for haptic guidance. When seen along the in-plane extension the guiding surface can have about constant normal extension height but can also have a variable height, e.g. for the purpose of guiding the haptic when the lens has a mobility in the normal direction. That the guiding surface has a "component" normal extension is meant to say that the guiding surface need not be perpendicular to the haptic plane but can have for example an inclination or curvature as well with respect to the normal direction. When seen along the guiding surface and in a direction in or parallel with the haptic plane, an inclination or ramped surface may serve for example to direct the haptic up or down in the normal direction, e.g. to deflect it towards a transfer slit. Similarly a curved or V-shaped profile may serve as a pocket to better fix or retain a haptic point on the guiding surface. The guiding surface can be positioned so as to contact points on the outer, convex, side of the haptic with the lens in the seat but is preferably so as to contact the inner, concave, side of the haptic. Nothing prevents that additional surface or surfaces are placed also on the convex side e.g. to stabilize the haptic or to creates slit between the guiding surface and the additional surface, preferably with a separation smaller than necessary for accommodation of the unstressed haptic, in order to assist in haptic stretching and retention in stretched condition, most preferably with a fairly narrow slit for the final shape of the haptic. At least one guiding surface should be present in the device and adapted for stretchin of one haptic leg. Typically lenses using spiraling type haptic use more than one leg, commonly two although three or more may be present. Preferably the present device contains two guiding surfaces, each adapted for stretching of different haptic legs, although more can be present in case of more than two haptic legs. Two guiding surfaces can be arranged with different spatial relationship to each other depending on the initial configuration and the final desired configuration. The initial configuration is not necessary defined by lens design in its unstressed condition. It is for example possible to have the optic part of the lens folded so as to make for example two diagonally arranged haptic attachments point in virtually any new angular relationship and similar results can be obtained by bending the mere haptic attachment. Accordingly two guiding surfaces can be arranged for final haptic configurations where the legs point in the roughly the same direction such as coinciding, parallel or with an acute angle therbetween, e.g. for the purpose of leaving the rear side of the lens free for abutment of a plunger or similar arrangements for final haptic configurations where the legs point in roughly opposite directions such as coinciding, parallel or with an obtuse angle therbetween, the latter e.g. for the purpose of keeping the trailing rear haptic slightly deflected out of direct abutment with a plunger in an implanter duct. However, for many purposes a preferred final configuration is with the haptic legs pointing substantially in opposite directions along lines being parallel or coinciding, e.g. compatible with implanter plungers partially or wholly enclosing the lens, rather than attacking its rear end, e.g. the paddle plunger types mentioned in the introduction. Although two or more guiding surfaces may be present they can be integrated in a monolithic structure, being separate but attached to each other or to a support, all giving the same function. Similarly the other device features to be described, disregarding those being movable with respect to the guiding surfaces, can be integral or attached to the guiding surfaces or its support.

The Seat

The minimum requirement on the seat is that it shall be able to accommodate the lens with the haptics in the described relationship to the guiding surfaces, preferably with the at least the haptics in unstressed or only slightly stressed condition. As indicated, the lens or haptic attachments can be folded or stressed although it is often preferred that also the lens is in the unstressed condition. With preference the seat can include a fixture for the purposes of facilitating proper placement of the lens, immobilizing the lens with respect to the seat and/or providing a support for movement of the lens. The arrangements for moving the lens, to be described, may require that the seat as such can be moved or that the fixture can be released or overcome. Fixation can be done by action on the lens optic part, e.g. by applying pressure substantailly transversal, i.e. perpendicular, to the lens plane e.g. by squeezing it between roof and floor of a seat chamber for example when closing a door to the chamber. Preferably then the lens can be initially slightly bent since then any rotation of the lens will be counteracted by the necessary change in deformation resulting from the change in fold line. For better control and leverage as well as for to impose rotation to the lens it is preferred to stabilize the lens haptics. This can be done by placing pressure transversal to the lens plane in a similar manner as described for the lens optic but it is preferred to arrange delimiting structures running in the transversal direction so as to stop or be active at lens rotation through abutment between haptic and the structure which can be used for all haptic types. Preferably at least two structures are used and most preferably arranged to prevent rotation on opposite directions, e.g. by holding one haptic on its both sides or by holding one haptic against rotation in one direction and a second haptic against rotation in the other direction. Most preferably two structures are used at each haptic, e.g. four structures for two haptics, two around both haptics, and arranged to counteract rotation in both directions at each haptic. For best stability the structures are preferably present close to the connection between haptic and optic. In addition the structures may be present all or the major part of the haptic periphery, e.g. to fully define their position, but it is often sufficient with point contact, e.g. from pins running transversely to the lens plane, at the described locations and a small size is also preferred when it is desirable to have facilitated disablement of the structures before lens displacement, in which connection the structures and lens should be moved in relation to each other to such an extent as to free the haptics for movement. When the guiding surfaces are arranged to contact the first point of the haptic at or close to its inner end the guiding surfaces can with preference act as the structures generally described above, e.g. providing one or two points of fixation contact for each haptic leg depending on whether one guiding surface is used alone or together with an additional surface, as described, respectively. The seat can be arranged fixed in relation to the guiding surfaces, e.g. when haptic stretching takes place without lens optic movement for example by manual or tool manipulation by stretching, drawing or pushing of the haptics along the guiding surfaces, preferably when the guiding surfaces are aligned with slits for transfer of the lens with stretched haptics to a secondary device such as an implanter duct. For reasons given it is in general preferred to perform haptic stretching by movement of the lens optic. This can still be done with a seat fixed in relation to the guiding surfaces, e.g. by manipulation of the lens in the seat, possibly assisted by a lubricant. Alternatively the seat can be a part separate from the guiding surfaces, e.g. a picking tool used to move the lens optic with respect to the guiding surfaces. Preferably such a movable seat has keying structures for cooperation with corresponding keying structures on or at the guiding surfaces or their support to thereby facilitate the manipulations, e.g. for placing and stabilization of the lens with respect to the guiding surfaces and preferably a lens guiding arrangement for the lens movement.

The Lens Guiding Arrangement

The lens guiding arrangement shall allow and preferably guide movement of the lens relative to the guiding surfaces along a path serving to stretch the haptics. This will require that the haptic curvature is reduced and normally also that at least a second point on each haptic leg comes into contact with, or closer to, the guiding surface. This may also mean that the first point moves away from the lens optic, e.g. when the first point is the free end and is maintained in contact with the guiding surface during stretching of the haptic, for example by pressing the haptic inner end towards the guiding surface. Alternatively the first point may go out of contact with the guiding surface, e.g. when the first point is close to the inner end of the haptic leg and stretching takes place by moving the first contact point outwards towards the free end, for example by letting the first point move along a ramped surface sloping away from the lens disc. Certainly it is also possible that several points on, stretches of or substantially the whole of the haptic leg come into contact or become lined up with the guiding surface. Various general movement patterns are possible to create the paths effective to stretch the haptics and will be described in general terms although it should be clear that various combinations of the general patterns are also possible. The movements are relative the guiding surfaces, which are supposed to be fixed. Movements will be described with respect to the optic part of a lens in unstressed condition, the rim of which optic part is supposed to lie in a lens plane and a lens axis is supposed to be normal to the lens plane and centered in the lens disc. For many common haptic designs the lens plane will be roughly coincide with the haptic planes, with the possible minor deviations earlier described. The lens may perform a rotation around an axis in the plane being a diagonal trough the optic part disc, which can be realized by lens guiding arrangement for example allowing rotation of the seat around such an axis, and used e.g. for straightening haptics pointing in opposite directions perpendicular to the axis, e.g. by gripping the haptic inner ends against guiding surfaces arranged in these directions and sloping out from the lens optic part when seen in the rotation direction. The lens may perform a movement within the lens plane. A first form of such a movement is a translation in the sense that the lens axis crossing with the plane also moves in the plane. The lens axis movement may be a circle, another curve or straight path, which can be realized by lens guiding arrangement for example in the form of a track for the seat in the plane, and used e.g. for straightening haptics having any of the parallel or angled relationships described. The movement in the lens plane can be a rotation around the fixed lens axis, which can be realized by lens guiding arrangement for example allowing rotation of the seat, and used e.g. for straightening haptics pointing in opposite directions e.g. by stopping the haptic free ends against the guiding surfaces. The lens movement be a displacement along the lens axis, which can be realized by lens guiding arrangement for example allowing the seat to move in a tube type channel, and used e.g. for straightening haptics pointing in any directions e.g. by gripping the haptic inner ends against guiding surfaces arranged in the desired directions and sloping out from the lens optic part when seen in the movement direction. In all embodiments the device preferably comprises handling features facilitating automated or preferably manual manipulation of the movable parts, e.g. press or rotation buttons, levers etc.

Auxiliary Features

With preference the device can include features assisting in other processing of the lens than haptic stretching. The device may act as a package for the lens in stressed or preferably unstressed condition for which purpose it may comprise parts that can be opened or ruptured. The device may include features for further processing of the lens after haptic stretching; in particular features lens compression to the reduced diameter and features for injection of the lens into an eye. Features for lens compression may include common types as described in the introduction, e.g. arrangements at or in the seat for sideways, or radial, squeezing in relation to haptic extension and lens injection, such as by use of "winged" and hinged half tubes. In addition or alternatively the device may include part of or a complete implanter duct, e.g. a duct embracing the seat, possibly with releasable fixation means for the lens, and the stretched haptics, the duct possibly including lateral opening or slits for reception of the haptics during stretching, the arrangement also allowing lens compression, or additional compression, in a converging channel in front of the seat. Alternatively the lens with stretched haptics can be transferred to an implanter duct, directly or via an intermediate duct, for the further steps. Unless the device and the implanter are integral, connecting features may be present for maintaining or locking, permanently or releasable, these parts to each other. Further a delivery opening on the device and a reception opening on the implanter may be needed. These should be mutually adapted to give a transfer opening, having the characteristics to be discussed below, either by having the same shape or by one having the necessary size and the other being oversized. The transfer opening can have general extension following the stretched haptic, e.g. a curved or straight slit for a partially and a fully stretched haptic leg respectively. Arrangements can be present for transfer of the haptics through the transfer opening, e.g. pushers for active transfer or guides, e.g. tapering surfaces on or at the guiding surfaces, for automatic guiding of the stretched haptics through the transfer opening during or after full stretching, possibly assisted by consumption of some of the stretching energy. It is preferred that also the lens optic is transferred to the implanter duct, requiring a transfer opening in size adapted to the lens width, e.g. by a delivery opening present under the seat. Although the lens can be transferred in unstressed condition it is preferred that the lens optic part is, or during transfer becomes, at least partially compressed, among others requiring smaller transfer opening and allowing transfer to a more narrow duct giving the stretched haptics less opportunity for re-coiling. In most cases it is preferred to orient the stretched haptic legs substantially along the implanter duct axis, possibly with minor deviations e.g. for adaptation to plunger design etc., also meaning a convenient axial orientation of an elongated reception slit. Substantially aligned forward and rearward directed haptics has also proved advantageous for reduce tendency to create a torque and optic rotation at implanter exit, especially when using the radial haptic anchoring principle, as defined, and most preferably if the lens is folded along a diameter passing through the anchoring points for two haptics. It is also preferred to include arrangements for closing the transfer opening after transfer of the lens to confine it in the receptacle during subsequent steps, e.g. until it has been moved out of the opening area, preferably by misaligning the delivery opening and reception opening such as by rotating the device relative the implanter. Although the variations described makes the device compatible with most implanter types, advantages are reached with implanters designed for lens charging in a direction lateral, or radial, with respect to duct axis and plungers carrying, rather than pushing, the lens such as those described having a lens enclosing flexible sheet or paddle, especially when adapted to be charged in a rear position and moved to a front position for lens injection into the eye.

The device can be manufactured in any material compatible with the lenses and able to sustain the fairly small forces involved. The materials can be similar to those used for implanters, such as glass, metal and preferably plastics. Suitable plastics are polyethylene, polypropylene, polycarbonate, polyamid, polymethylmethacrylate, PET, PBT, PEI, PES, PPO, POM, GPPS etc. It may preferred to select a transparent material to allow the operator monitoring the lens and haptic behavior. The preferred manufacturing method is injection molding. For example for the purpose of protecting the lens and facilitating its movement or transfer surfaces in contact with the lens can be coated or chemically modified to reduce friction against the lens, e.g. glycerin, monoglycerol stearate, silicone, polytetrafluoroethylene or hydrophilic coatings of polymers or hydrogels. An eye surgically acceptable lubricant can also be used on the lens or in the duct, e.g. a viscoelastic composition such as Healon®.

Use Method

How to use the device has been described above in connection with each device feature. Before the surgical situation the device can be prepared in various ways. The lens can be pre-loaded into the device and sterilized at a manufacturing site for storage and stored and transported within the device, which may be of particular interest in connection with disposable devices, preferably in substantially unstressed condition in order to avoid gradual permanent deformation. Alternatively the lens may be charged into the device in connection with use, which may be of interest for reusable devices. An operator may introduce the lens in naked form, e.g. by use of forceps, only by placing it on the device seat and possibly controlling that each haptic first point is properly positioned. Alternatively the lens may be introduced pre-loaded on a seat cassette, e.g. to allow adaptation between seat and lens for different lens haptic types or optic types, e.g. in respect of varying diopters etc.

SUMMARY OF DRAWINGS

FIG. 1 depicts schematically various aspects of a lens with spiraling haptics. FIG. 1A is a plan view, FIG. 1B a side view and FIG. 1C and FIG. 1D show two different folding patterns.

FIG. 2 depicts schematically various basic principles for haptic stretching according to the invention. FIGS. 2A and 2B show in plain view haptic stretching, in early and late stages respectively, based on lens rotation in the lens optic plane. FIGS. 2C and 2D show in side view haptic stretching, in early and late stages respectively, based on lens movement along lens optic plane normal. FIGS. 2E and 2F show adaptations for lenses folded as in FIGS. 1C and 1D respectively.

FIG. 3 illustrates schematically a tube-shaped duct with a slit arranged to receive a lens with pre-stretched haptics.

FIGS. 4A and 4B show a first preferred embodiment based on lens movement along lens optic plane normal.

FIG. 5 shows a drawing of a second preferred embodiment based on rotation of the lens in the optic plane. FIG. 5B shows the assembled device in an initial condition before haptic stretching and FIG. 5C shows the device in a final state after haptic stretching.

DESCRIPTION OF DRAWINGS

Figure 5A:
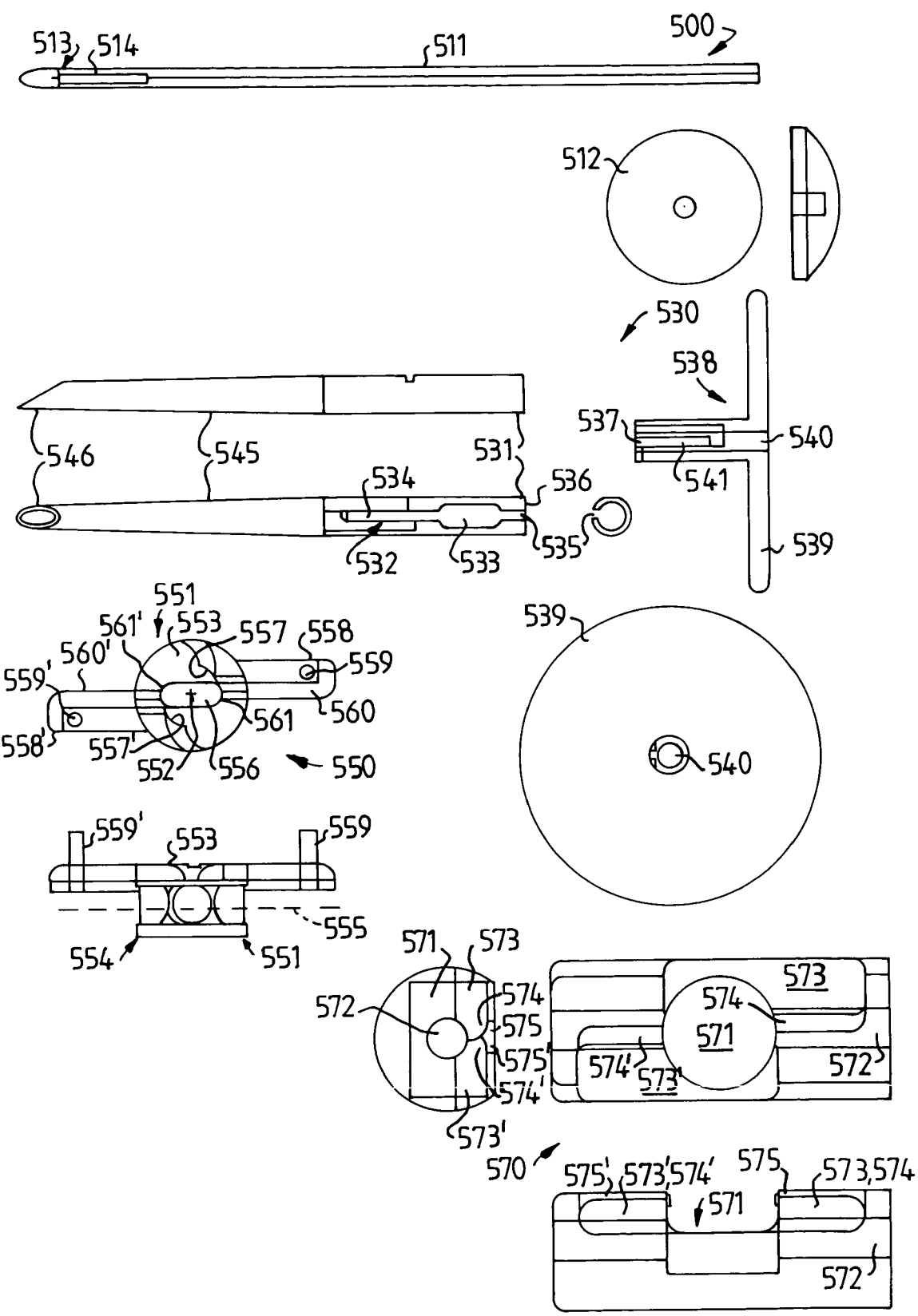
FIG. 5A is an exploded view of the device parts.

FIG. 1 depicts schematically various aspects of a lens with spiraling haptics in unstressed condision. FIG. 1A is a plan view, FIG. 1B a side view and FIG. 1C and FIG. 1D show two different folding patterns for the optic part. The lens 1 has a disc shaped optic part 2 and two haptic legs 3 and 3', having inner ends 4 and 4' attached to the optic 2 and outer free ends 5 and 5' and being curved to as to have concave inner sides 6 and 6' and convex outer sides 7 and 7'. The lens optic part defines an optic plane, which in FIG. 1A is supposed to coincide with the Figure plane. In the side view of FIG. 1B, the optic plane is supposed to be normal to the Figure plane and is shown with dotted line 10. An optic plane normal 11 cuts through the optic disc center. Also the points along the haptics 3 and 3' are supposed to roughly fall in haptic planes 12 and 12', also having haptic plane normals 13 and 13', although only one haptic plane is shown in FIG. 1B. Numerous haptic designs are known and theoretically the haptic planes can be curved in various manners although for present purposes the planes can be treated as roughly flat. Such haptic planes can coincide or be parallel with the optic plane although it is also common that they have a slightly angled orientation, as indicated by the tilt of haptic plane normal 13, 13', to create an overall asymmetric lens. In FIG. 1A is indicated two possible fold lines 8 and 9 respectively for the optic part of the disc. Fold line 8 runs at about a right angle to a diagonal between inner points 4 and 4' and produces the structure in FIG. 1C with the inner points 4 and 4' close to each other and may be useful for final stretched haptics pointing in the same direction, e.g. forwards in an implanter duct. Fold line 9 runs at about an about 45 degree angle to a diagonal between inner points 4 and 4' and produces the structure in FIG. 1D with the inner points 4 and 4' at a position intermediate between the maximum and minimum distances possible and may be useful for final stretched haptics pointing in different directions, e.g. forwards and rearwards in an implanter duct but with central parts free for example for a plunger and without colliding the haptics.

FIG. 2 depicts schematically various basic principles for haptic stretching according to the invention by movement of the lens relative guiding surfaces, which movements may take place without, but preferably with, lens seats and lens guiding arrangements, not emphasized in these Figures. FIGS. 2A and 2B show in plain view haptic stretching, in early and late stages respectively, based on lens rotation in the lens optic plane. In FIG. 2A the free ends 5 and 5' of haptics 3 and 3' have contact with guiding surfaces 20 and 20' repectively. To stretch the haptics the lens 2 is rotated around its axis 11 as indicated by arrow 21. During such rotation both haptics will simultaneously be stretched to a the less curved configuration shown in FIG. 2B whereat the contact points between free ends 5 and 5' and guiding surfaces 20 and 20' will move somewhat radially outwards with respect to the optic 2.

FIGS. 2C and 2D show in side view haptic stretching, in early and late stages respectively, based on lens movement along lens optic plane normal 11. In FIG. 2C the inner ends 4 and 4' of haptics 3 and 3' have contact with guiding surfaces 22 and 22' repectively, having cam surfaces 23 and 23' sloping radially away from the lens optic 2 from innermost points 24 and 24' and outwards, when seen in the lens movement direction as indicated by arrow 25. The haptics are placed so that the guiding surfaces innermost point 24 and 24' becomes situated at the concave side of the haptics 3 and 3' and at or in contact with the inner ends 4 and 4' so that the haptics curl around the innermost points 24 and 24'. To stretch the haptics the lens 2 is is moved down along arrow 25, without rotation around its axis 11. During such movement the contact points between the haptics and the cam surfaces 23 and 23' will move outwards, from the initial contact point at inner end 4 and 4', and both haptics will simultaneously be stretched to a the less curved configuration shown in FIG. 2D, also illustrating the use of an optional additional surface 26 placed on the convex side of the haptic to create a slit for the haptic 3. FIG. 2E shows in view from above a similar situation as in FIG. 2C although adapted for a folded lens as in FIG. 1C. Guiding surfaces 22 and 22', with their respective cam surfaces 23 and 23', are here placed in parallel so that in the initial state their innermost points 24 and 24' becomes located on the concave sides close to the inner ends 4 and 4' of haptics 3 and 3', located close to each other due to folding along line 8. FIG. 2F shows a similar modification for the lens folded according to FIG. 1D along fold line 9 to give an initial angular relationship between haptics 3 and 3'. Guiding surfaces 22 and 22', with their respective cam surfaces 23 and 23', are here placed in a corresponding angled relationship to illustrate the flexibility in the stretching pattern.

FIG. 3 illustrates schematically a tube-shaped duct, e.g. part of an implanter duct, with a slit arranged to receive a lens with haptics pre-stretched according to the any of the methods outlined. The tube 30 has a generally straight and axial slit 31, having narrow forward 32' and rearward 32 sections, adapted to receive the stretched haptics and an enlarged intermediate section 33, adapted to receive the lens optic disc, the extension of which is indicated by phantom line 34. Since the optic diameter is larger than the width of the midsection it is clear that certain folding of the lens optic is needed when moving it through the slit.

FIGS. 4A and 4B illustrates a preferred system embodiment of the invention based on lens movement along lens optic plane normal. The system, generally designated 400, comprises a lens package 410, a lens picker 420 and a combination 440 of lens implanter and haptic stretching device. As illustrated in FIG. 4A the lens 411 is delivered in a package 410 from which it can be removed after opening or removal of a closure (not shown). The lens can be picked from the package by use of the picker 420, which can be regarded as a seat for the lens, in this case simply by adhering it to the picker lower end 421 to which has been applied a drop of viscoelastic fluid. Alternatively the picker may include other lens gripping means such as a slight vacuum created by retraction of a plunger or membrane behind a gripping opening or by forceps like extensions. With preference the lens package may include (not shown) a lens fixture for keeping the lens in a predetermined orientation as well as key structures in the package and on the picker to secure that the lens will have a suitable initial orientation on the picker, preferably with the haptic inner points 412 and 412' become aligned under fins 422 and 422' extending in straight opposite directions radially out from a central stem 423. The picker further comprises a fixed finger-grip 424 and a movable button 425 attached to a rod 426 movably arranged axially within the stem for exposure at the picker lower end 421 to release and push the lens 411 to be described. In FIG. 4B the picker 420 with attached lens is shown above the combination device 440 in an initial position ready for subsequent steps. The combination can be said to comprise an implanter part 441 and an haptic stretcher part 450. The implanter part is shown with a rear part 442 comprising any type of lens advancing mechanism (not shown), a generally tubular intermediate part 443 for reception of a lens with stretched haptics and partially folded or compressed optic and a tip part 444 for insertion into the eye and release of the lens, the tip part being attached to the intermediate part and having a convergent duct part for further compression of the lens. The intermediate part 443 has a reception opening for the lens in the form of rear and front slits 445 and 445' for the haptics joined at an enlarged intermediate section (not shown) for the optic part. The haptic stretching part 450 has guiding surfaces 452 and 452' similar to those shown in FIG. 2C, with sloping cam edges 453 and 453' an innermost crest points 454 and 454'. The guiding surfaces 452 and 452' are designed as flat extensions on half-tube parts 455 and 455', together forming a channel 456 for the lens movement, to be described. A separation is present between the half-tube ends 457 and 457' and the opposing guiding surfaces 452' and 452 respectively, allowing passage of the haptics and picker fins 422 and 422' during stretching. The separations continue into the slits 445 and 445' in the intermediate part 443 of the implanter part 441 whereas the channel continues in the enlarged intermediate section of the intermediate part. In operation the picker is simply moved axially down in the direction of the arrow 427 so as to guide fins 422 and 422' into the separations between guiding surfaces 452 and 452' and half-tube ends 457' and 457 respectively. During this lens movement the crests 454 and 454' and/or cam surfaces 453 and 453' will first engage the lens haptics at their inner concave side and close to their inner ends and during further movement the cam surfaces 453 and 453' will engage points on the haptic legs towards their free ends under stretching until the haptics are stretched and aligned over the slits 445 and 445', which can be regarded at the end of the haptic stretching phase under which the channel 456 and the picker 420 can be regarded as lens guiding arrangement for the lens movement. Continued movement can be regarded representing a lens transfer phase in which the haptics passes through the slits under assistance of the size adapted fins 422 and 422' and the lens optic part under folding and compression is forced into the implanter enlarged intermediate section under assistance of rod 426, exposed by manual pressure on button 425. Although the stretching and transfer phases have been described as separate and sequential actions, it is equally possible and within the inventive concept that they occur simultaneously or overlapping, e.g. by part of the haptics finding their way through the slit under the stretching operation.

FIG. 5 shows a drawing of a second preferred embodiment based on rotation of the lens in the optic plane. FIG. 5A is an exploded view of the device parts, FIG. 5B shows the assembled device in an initial condition before haptic stretching and FIG. 5C shows the device in a final state after haptic stretching. Referring first to FIG. 5A, the device, generally designated 500 can be said to comprise a plunger unit 510, an implanter unit 530 and a haptic stretching device comprising a lens seat part 550 and a support part 570. The plunger unit 510 comprises a rod 511 to the rear end of which is attached a press button 512 and to the front end of which is attached a lens engaging part 513, here shown as a foldable paddle type sheet 514 in its folded state. The implanter 530 comprises a generally tubular lens receiving mid-section 531, having a slit 532, forming a reception opening for the lens, the slit having a wide middle part 533 for the lens optic, a narrow front part 534 for a forward pointing haptic and a narrow rear part 535 for a rearward pointing haptic. The rear end 536 of the mid-section 531 is attached to the front end 537 of an end piece 538, also having a rear finger-grip 539 and a central channel 540 for insertion of the plunger rod 511. The channel 540 has a slit 541 forming a direct continuation of the narrow rear slit part 535 when the end piece 538 is joined to the mid-section 531. In the forward direction the mid-section continues in tip part 545, which is generally tubular and slightly converging for further compression of the lens when passed through the tip part. The tip part ends in a beveled opening 546 for release of the lens when inserted into an eye. The seat part 550 comprises a central cylindrical part 551, rotational around its concentric axis 552 when inserted into the support 570, to be described. The upper part 553 of the cylinder acts as the lens seat proper whereas the lower part 554 of the cylinder stabilizing rotor when assembled with the support. Except for the lowermost plate, the lower part is a quite open, cage-like, structure designed to accommodate the implanter mid-section 531 along axis 555 all over the cylinder rotation angles between its initial position and its final position, as illustrated in FIGS. 5B and 5C. The cylinder upper part 553 has a central delivery opening 556, having a length roughly corresponding to the diameter of the lens optic part but being narrower in width, meaning that the lens becomes folded when forced through the delivery opening. When inserted in the support and with the seat moved to its final position the delivery opening 556 becomes positioned over, and aligned in parallel with, the reception opening 533 of the implanter mid-section 531. Lens fixture structures 557 and 557' raises above the lens position and from these extend two arms 558 and 558' with maneuvering pins 559 and 559' to assist manual rotation. The arms 558 and 558' have inner ends 560 and 560' the height and curvature of which, when seen in cross-section, are adapted to fill out corresponding pockets on the support to be described. The intersections 561 and 561' between lens fixture structures 557 and 557' and the inner ends 560 and 560' of the arms respectively forms haptic attack points, engaging the haptics at their inner ends during rotation to thereby also rotate the lens optic. The support 570 comprises a central cylindrical bore 571, designed to act as a bearing for the cylinder lower part 554 of the seat. It also has an implanter channel 572 designed to receive the mid-section 531 of the implanter, also passing through the seat cylinder lower part 554 along axis 555 when inserted in the support. The support also has two cutouts 573 and 573' adapted to the shape of the arms 558 and 558' and allowing them to move between the positions shown in FIGS. 5B and 5C respectively. The inner parts of the cutouts 573 and 573' forms haptic pockets 574 and 574' under roofs 575 and 575', which roofs in the pockets slopes inwards and downwards towards the far end of slits 534 and 535 of the implanter mid-section 531 when attached to the support. The inner ends 560 and 560' of the arms are adapted to substantially fill up the pockets 574 and 574' in the final position shown in FIG. 5C. All this serve to safely guide the haptics towards and through the slits during the stretching operation. The device can preferably be assembled by inserting the cylinder lower part 554 of seat 550 into cylindrical bore 571 of support 570. Then the implanter is inserted through channel 572 and trough seat cylinder lower part 554 along axis 555 to locate the mid-section 531 so as to locate the slit wide middle part 533 central in the cylinder bore 571 for which suitable stop surfaces can be present (not shown). The implanter part can in assembled or disassembled form when this is done but final operation requires that the end piece 538 is attached to the rear end 536 of the mid-section 531 and the plunger rod 511 is inserted into finger-grip 539 central channel 540 and attached to its button 512. The assembled device is shown in FIGS. 5B and 5C. The discussion of details will be restricted to those needed for explanation if its use. The lens is placed in the seat when the arms 558 and 558' have the position shown in FIG. 5B. The lens 580 is positioned with its optic part 581 concentric on the seat cylinder upper part 553, which is facilitated by lens fixture structures 557 and 557'. The free ends of lens haptic legs 582 and 582' are placed or becomes placed at or in support pockets 574 and 574' whereby the inner ends of the haptic becomes positioned at or in contact with the haptic attack points at the intersections 561 and 561'. From this situation the arms 558 and 558' are simply rotated in the direction of arrows 584 and 584', which will straighten the haptics and give the final arrangement shown in FIG. 5C. Here the arms 558 and 558' has moved into and over the cutout areas 573 and 573' and the inner ends 560 and 560' of the arms fills out the pockets 574 and 574' of the support, which assist to bring the haptics 582' and 582 through the slits 534 and 535 with its extension 541 respectively. If pressure is applied on the lens optic 581 at its central part it will fold and pass through the delivery opening 556 of the seat, through the reception opening 533 and into the implanter for rest on the plunger foldable paddle sheet 514. If desired the finger-grip 539 and support 570 can now be mutually rotated to thereby misalign the delivery opening 556 and reception opening 533 to close the transfer opening. The implanter can then be used conventionally, i.e. by forward movement of the plunger rod 511 the lens is moved under compression through the tip 545 up to the beveled opening 546 in a position ready for injection. If desired the support 570 and seat 550 assembly can now be removed to make the implanter device more handy in the final surgical operations.

The invention claimed is:

1. A device for stretching haptics of a deformable intraocular lens, the lens in un-deformed state comprising a) a roughly disc shaped optic part defining an optic plane and a concentric optic axis normal to the plane, configured to act as a lens when inserted into an eye, and b) at least two elongated haptic legs, each leg having an inner end attached to the optic part, an outer end being free and intermediate points in between the inner end and the free end, each leg being curved in an unstressed state, the curvature defining a curve plane for each leg, and being flexible to at least a less curved configuration under stress, the device comprising i) at least two haptic guiding surfaces respectively arranged for at least two haptic legs, ii) a seat arranged with respect to the guiding surfaces so as to allow, when a lens is positioned in the seat, contact between a first point on each leg and its corresponding guiding surface, and iii) a lens guiding arrangement operable to allow a lens positioned in the seat to be moved along a path in the optic axis direction to bring at least a second point on each leg into contact with, or closer to, its corresponding guiding surface, to orient each leg to a less curved state, wherein the guiding surfaces have a height which covers at least a part of the path in the optic axis direction and which decreases in directions out from the seat.

2. The device of claim 1, wherein the guiding surfaces are substantially straight.

3. The device of claim 1, wherein the guiding surfaces are positioned so as to contact an inner, concave, side of respective legs.

4. The device of claim 3, wherein one or more additional surfaces are positioned so as to contact a convex side of a leg.

5. The device of claim 1, wherein two guiding surfaces are arranged in an angled relationship.

6. The device of claim 1, wherein two guiding surfaces are arranged in a coinciding, parallel or aligned relationship.

7. The device of claim 6, wherein the two guiding surfaces point substantially in opposite directions.

8. The device of claim 1, wherein the guiding surfaces are arranged fixed in relation to each other.

9. The device of claim 1, wherein the seat is arranged to accommodate the lens optic in substantially unstressed condition.

10. The device of claim 1, wherein the lens guiding arrangement is arranged to reduce the curvature between the first point and the second point during lens movement.

11. The device of claim 1, wherein the seat is arranged movable in the optic axis direction.

12. The device of claim 11, wherein the seat is arranged movable in a channel.

13. The device of claim 1, wherein the device is adapted to act as a package for the lens in stressed or unstressed condition.

14. A combination, comprising the device of claim 1, and a receptacle, wherein the device is arranged for transfer of the lens with stretched legs to the receptacle.

15. The combination of claim 14, wherein a delivery opening is arranged on the device and a reception opening is arranged on the receptacle, the delivery opening and reception opening being connectable to form a transfer opening for transfer of the lens.

16. The combination of claim 15, wherein the transfer opening is elongated and adapted for passage of the stretched legs and the optic.

17. The combination of claim 16, wherein the transfer opening is narrower than the lens optic in unstressed state.

18. The combination of claim 14, wherein the receptacle is generally tube shaped with an interior duct, defining a duct axis.

19. The combination of claim 18, wherein a transfer opening extends on the tube periphery substantially parallel with the duct axis.

20. The combination of claim 18, wherein the duct diameter is less than the unstressed optic diameter.

21. The combination of claim 14, wherein the receptacle is an implanter, or part of an implanter, adapted for insertion of the lens into the eye.

22. The combination of claim 21, wherein the implanter has a plunger arrangement for moving the lens.

23. The device of claim 1, wherein the device comprises handles for facilitating manual manipulation of a lens along the path.

24. The device of claim 1, wherein the device is adapted to act as a package for a lens in unstressed condition.

25. A combination, comprising the device of claim 1 and a deformable intraocular lens, the lens in un-deformed state comprising a) a roughly disc shaped optic part defining an optic plane and a concentric optic axis normal to the plane, configured to act as a lens when inserted into an eye, and b) at least two elongated haptic legs, each leg having an inner end attached to the optic part, an outer end being free and intermediate points in between the inner end and the free end, each leg being curved in an unstressed state, the curvature defining a haptic curve plane for each leg, and being flexible to at least a less curved configuration under stress, wherein the guiding surfaces have less curvature than the legs in the unstressed state.

26. The combination of claim 25, wherein the guiding surfaces have extensions in the haptic planes corresponding with the whole length between the inner end and the free end of the respective leg.

27. The combination of claim 25, wherein the guiding surfaces have extensions in the haptic planes covering a length corresponding to the respective leg length in the stretched straight condition.

28. The combination of claim 25, wherein the first point is close to the leg inner end.

29. A device for stretching haptics of a deformable intraocular lens, the lens in un-deformed state comprising a) a roughly disc shaped optic part defining an optic plane and a concentric optic axis normal to the plane, configured to act as a lens when inserted into an eye, and b) at least two elongated haptic legs, each leg having an inner end attached to the optic part, an outer end being free and intermediate points in between the inner end and the free end, each leg being curved in an unstressed state, the curvature defining a curve plane for each leg, and being flexible to at least a less curved configuration under stress, the device comprising i) at least two haptic guiding surfaces respectively arranged for at least two haptic legs, ii) a seat arranged with respect to the guiding surfaces so as to allow, when a lens is positioned in the seat, contact between a first point on each leg and its corresponding guiding surface, and iii) a lens guiding arrangement operable to allow a lens positioned in the seat to be moved along a path in the optic axis direction to bring at least a second point on each leg into contact with, or closer to, its corresponding guiding surface, to orient each leg to a less curved state, wherein the seat is a part separate from the guiding surfaces and includes a securement structure, wherein the device includes corresponding structures on or at the guiding surfaces or a support for the guiding surfaces, wherein the securement structure and the corresponding structures are operable to cooperate to secure a lens in an orientation and wherein the seat securement structure comprises a pair of guide fins adapted to cooperate with separations between the guiding surfaces to orient the lens.

30. A combination, comprising the device of claim 29 and a deformable intraocular lens, the lens in un-deformed state comprising a) a roughly disc shaped optic part defining an optic plane and a concentric optic axis normal to the plane, configured to act as a lens when inserted into an eye, and b) at least two elongated haptic legs, each leg having an inner end attached to the optic part, an outer end being free and intermediate points in between the inner end and the free end, each leg being curved in an unstressed state, the curvature defining a haptic curve plane for each leg, and being flexible to at least a less curved configuration under stress, wherein the guiding surfaces have less curvature than the legs in the unstressed state.

* * * * *